(12) United States Patent
Takegoshi et al.

(10) Patent No.: US 8,798,949 B2
(45) Date of Patent: Aug. 5, 2014

(54) SPECTROMETER, MEASURING APPARATUS, AND METHOD OF DATA PROCESSING

(75) Inventors: Kiyonori Takegoshi, Kyoto (JP); Yusuke Nishiyama, Akishima (JP)

(73) Assignee: JEOL Resonance Inc., Tokyo (JP)

( * ) Notice: Subject to any disclaimer, the term of this patent is extended or adjusted under 35 U.S.C. 154(b) by 359 days.

(21) Appl. No.: 13/109,165

(22) Filed: May 17, 2011

(65) Prior Publication Data

US 2011/0288802 A1 Nov. 24, 2011

(30) Foreign Application Priority Data

May 19, 2010 (JP) ................................ 2010-115597

(51) Int. Cl.
  *G06F 19/00* (2011.01)
  *G01N 24/08* (2006.01)
  *G01R 33/46* (2006.01)
  *G01R 33/56* (2006.01)

(52) U.S. Cl.
  CPC .... *G01R 33/4625* (2013.01); *G01N 2201/1245* (2013.01); *G01N 24/08* (2013.01); *G01R 33/5608* (2013.01)
  USPC .............................. 702/76; 324/307; 324/316

(58) Field of Classification Search
  CPC ........ G06F 19/00; G01N 33/48; G01N 33/50; G01N 33/543
  USPC ...................... 702/76; 324/310, 314, 31, 307
  See application file for complete search history.

(56) References Cited

U.S. PATENT DOCUMENTS

| 3,824,451 | A  | * | 7/1974  | Freeman et al. ............... 324/312 |
| 4,642,778 | A  | * | 2/1987  | Hieftje et al. .................... 702/23 |
| 6,081,119 | A  |   | 6/2000  | Carson et al. |
| 2004/0098208 | A1 | * | 5/2004 | Reeve et al. ..................... 702/32 |
| 2006/0241382 | A1 | * | 10/2006 | Li et al. ......................... 600/410 |

FOREIGN PATENT DOCUMENTS

EP 1304582 A1 4/2003

OTHER PUBLICATIONS

Fukazawa, et al., "Phase covariance in NMR signal", Physical Chemistry Chemical Physics, Aug. 17, 2010.*
C. Broeckling, et al., "MET-IDEA: Data extraction tool for mass spectrometry-based metabolomics", Analytical Chemistry, vol. 78, No. 13, Jul. 1, 2006.*
Takeuchi et al., "C13 NMR, Fundamentals and Applications (in Japanese)", Kodansha Ltd., Nov. 1, 1976, pp. 145-148.
Levitt, "Spin Dynamics: Basics of Nuclear Magnetic Resonance", John Wiley & Sons, Ltd, 2008, pp. 86-89.

* cited by examiner

*Primary Examiner* — John Breene
*Assistant Examiner* — Ruihua Zhang
(74) *Attorney, Agent, or Firm* — The Webb Law Firm

(57) ABSTRACT

A spectrometer has: Accumulation means to obtain a data set containing N data points, repeating the measurement M times to obtain M spectral data sets or time-domain data sets S1 (d1 to dN) to SM (d1 to dN), and accumulating the M spectral data sets or time-domain data sets. Means for creating sets S1 (dn) to SM (dn) of the data points contained in the M spectral data sets or time-domain data sets S1 (d1 to dN) to SM (d1 to dN). Correlation computing means for finding correlations. Computing means for finding either the product of an accumulated or anticipated spectrum.

5 Claims, 9 Drawing Sheets

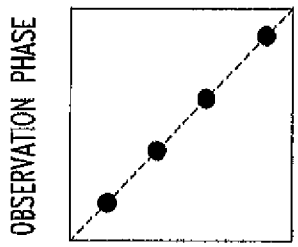
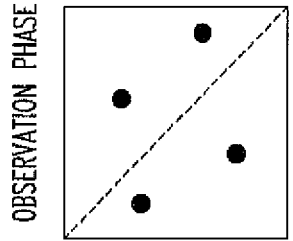
SIGNAL PHASE
AT POSITION A
SIGNAL PHASE
AT POSITION B
FIG.8A
FIG.8B
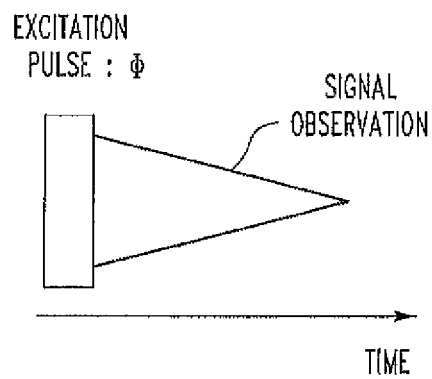
FIG.9

SPECTROMETER, MEASURING APPARATUS, AND METHOD OF DATA PROCESSING

BACKGROUND OF THE INVENTION

1. Field of the Invention

The present invention relates to a data processing method used in the field of spectroscopy and capable of providing improved signal-to-noise ratio (S/N). The invention also relates to a spectrometer and a measuring apparatus operating based on the data processing method.

2. Description of Related Art

A nuclear magnetic resonance (NMR) spectrometer is now described as one example of spectrometer. The NMR spectrometer is an apparatus for analyzing the molecular structure of a sample placed within a static magnetic field by irradiating the sample with pulsed RF waves having the NMR frequency of the nuclei to be observed, then detecting a feeble RF signal (NMR) signal emanating from the sample, and extracting molecular structure information contained in the detected signal.

FIG. 1 is a schematic block diagram of an NMR spectrometer. This instrument includes an RF pulse generator 1 that generates RF pulses having the NMR resonance frequency of nuclei under observation. The generated RF pulses are so controlled as to have a specified RF phase $\phi$, a specified pulse width, and a specified amplitude value. The RF pulses are fed to an NMR probe 4 via an RF amplifier 2 and a duplexer 3. Then, the RF pulses are applied to a sample under investigation from an irradiation/detection coil (not shown) placed within the probe 4.

After the RF pulse irradiation, a feeble NMR signal (free induction decay (FID) signal) produced from the sample is detected by the irradiation/detection coil and then fed via the duplexer 3 to a preamplifier 5, where the signal is amplified. Then, the signal is furnished to a receiver 6.

An FID signal in the audio-frequency range is obtained by demodulation performed in the receiver 6 and converted into a digital signal by an analog-to-digital converter 7. The digital signal is then fed to a control computer 8.

The control computer 8 supplies control signals to the RF pulse generator 1 to specify the RF phase $\phi$, pulse width, and amplitude value. The computer 8 also Fourier transforms the FID signal accepted in the time domain into NMR spectral data in the frequency domain and displays the data as an NMR spectrum. If necessary, the computer makes a phase correction of the NMR spectrum. In practice, real-part and imaginary-part spectra are obtained as the NMR spectrum. Usually, the real-part spectrum is displayed as an NMR spectrum.

In such an NMR instrument, the sensitivity for NMR signals are expressed by the ratio of signal to noise, abbreviated as S/N. Heretofore, various approaches have been used to improve the S/N. The approaches can be classified into a technique for suppressing noise, a technique for increasing the signal intensity, and a technique for discriminating noise and signal from each other. A well-known technique most relevant to the present invention is the technique for discriminating noise and signal from each other.

The most widely accepted method of the techniques classified as the approach for discriminating noise and signal from each other is known as accumulation. That is, plural NMR signals are observed and summed up to thereby increase the signal intensity relative to noise. Consequently, the signal is enhanced, and a high-sensitivity NMR spectrum is obtained.

The key concept of this technique is that when plural measurements are made and the obtained signals are summed up, the signal increases in proportion to the number of measurements, while the noise increases in proportion to ½ power of the number of measurements. For example, if two measurements are made and the resulting signals are summed up, the signal is directly doubled. In contrast, the noise increases by a factor of $2^{1/2}$ (about 1.4). When two measurements are made in this way, the signal is augmented relative to the noise. The sensitivity for NMR spectra, i.e., S/N, is increased by a factor of about 1.4.

Generally, if n accumulation steps are performed, the S/N is improved by a factor of $n^{1/2}$. It is very easy to perform an accumulation operation and thus accumulation has been used for many years as a technique for improving the S/N. Furthermore, accumulation is a simple additive operation and, therefore, it is easy to realize it by a hardware configuration. Also, it is not necessary to increase the capacity of a memory used to hold measurement results. In this way, accumulation is an intuitive technique which is easy to implement and which covers a wide range of applications. Today, accumulation is a technique routinely used in spectrometers such as FT-IR, as well as in NMR. Where S/N is not sufficiently high, accumulation is an approach employed almost always. (See "C13 NMR, Fundamentals and Applications (in Japanese)", written by Yoshito Takeuchi and Hidehiro Ishizuka, supervised by Shizuo Fujiwara, edited by Kodansha Scientific, published on Nov. 1, 1976, by Kodansha Ltd., pp. 145-148.)

Accumulation is a technique that is quite easy to use but it is said that there is the problem that the signal-to-noise ratio is not improved much when compared with the time taken for measurements. For example, if 16 accumulation steps are performed, the signal-to-noise ratio is improved by a factor of $16^{1/2}=4$. That is, the signal-to-noise ratio is improved only by a factor of 4 though the measurement time is prolonged as long as 16 fold. If an accumulation operation is performed over the whole one day (24 hours) to improve the sensitivity, the sensitivity improvement is as small as four times compared with an accumulation operation performed for 1.5 hours.

In this way, where accumulation is applied, there is the problem that a very long measurement time is required to improve the signal-to-noise ratio and that the rate of improvement is not very good. We have considered that this problem arises from the fact that only the difference between the manner in which signal increases by a factor of n and the manner in which noise increases by a factor of $n^{1/2}$, where n is the number of accumulation steps, is noticed in the accumulation technique in discriminating signal and noise.

More specifically, when the same measurement is repeated, the signal always produces the same result. On the other hand, noise produces random values. This feature has not been noticed sufficiently. When accumulation steps are performed, signal and noise behave differently. We have thought that if this is utilized, it is possible to develop a more effective method of discriminating signal and noise from each other.

SUMMARY OF THE INVENTION

In the present invention, in order to discriminate signal and noise from each other, the signal-to-noise ratio is improved by an accumulation technique. In addition, signal and noise are discriminated more conspicuously from each other by taking notice of other parameters. Consequently, a spectrum with a greatly improved S/N is obtained.

To achieve this object, the present invention provides a spectrometer comprising: accumulation means for accumulating M spectral data sets or time-domain data sets S1 (d1 to dN) to SM(d1 to dN) obtained by repeating the same measurement M times, each of the data sets having N data points; correlation computing means for finding correlations between the sets S1(dn) to SM(dn) of data points which are contained in the M spectral data sets or time-domain data sets S1(d1 to dN) to SM(d1 to dN), each of the sets S1(dn) to SM(dn) having data points of the same ordinal number dn, to thereby find a correlation data set C(c1 to cN) indicating correlation strengths about the data points of the ordinal numbers; and computing means for finding the product of an accumulated or anticipated spectral data set or a time-domain data set Sav(d1 to dN) having the N data points and obtained from the accumulation means and the correlation data set C(c1 to cN).

In one feature of the invention, the spectrometer is an NMR spectrometer, an ESR spectrometer, an electromagnetic spectrometer employing X-rays, ultraviolet rays, visible light, infrared radiation, microwaves, or radio waves, a mass spectrometer, an instrument utilizing a charged-particle beam (including an electron microscope), or an imaging apparatus employing any of such instruments.

A measuring apparatus according to the present invention comprises: means for creating M data sets S1 (d1 to dN) to SM (d1 to dN) by repeating a measurement while varying at least one measurement parameter in M increments, each of the data sets having N data points; means for creating sets S1 (dn) to SM (dn) of the data points contained in the M data sets S1 (d1 to dN) to SM (d1 to dN) such that the data points of each one of the sets S1 (dn) to SM (dn) have the same ordinal number dn; correlation computing means for finding a correlation data set C(c1 to cN) indicating correlation strengths about the data points of the ordinal numbers by finding correlations between data representing variations forecasted in response to variations in the parameter regarding the sets S1(dn) to SM(dn); and computing means for finding a product of an accumulated or anticipated data set Sav(d1 to dN) which has N data points and which is obtained by an accumulation operation after correcting effects of variations in the parameter regarding the data sets S1(d1 to dN) to SM(d1 to dN) and the correlation data set C(c1 to cN) or a product of a separately measured data set So(d1 to dN) and the correlation data set C(c1 to cN).

In another feature of the invention, the spectrometer is an NMR spectrometer, an ESR spectrometer, an electromagnetic spectrometer employing X-rays, ultraviolet rays, visible light, infrared radiation, microwaves, or radio waves, a mass spectrometer, an instrument utilizing a charged-particle beam (including an electron microscope), or an imaging apparatus employing any of such instruments.

In a further feature of the invention, the measuring apparatus is an NMR spectrometer. For each combination of the varied parameter and the data between which correlations are to be found, the correlation strength is found in at least one of the following cases: (1) the parameter is the phase of a reference wave for a receiver system for observing an NMR signal or the phase of an excitation RF wave for observing nuclei under observation and the data between which correlation should be found is the phase at each data point of an actually measured NMR signal; (2) the parameter is the strength of the exciting RF wave and the data between which correlation strength should be found is the strength of each data point of an actually measured NMR signal; and (3) the parameter is the center frequency of the exciting RF wave and the data between which correlation should be found is the frequency position at which an actually measured NMR signal appears.

The aforementioned correlation strength is found regarding data measured in relation to a direct observation axis in one-dimensional NMR measurements or regarding data obtained in relation to an indirect observation axis in multi-dimensional NMR spectroscopy.

A method of processing data in accordance with the present invention starts with repeating the same measurement M times to obtain either M spectral data sets or time-domain data sets S1(d1 to dN) to SM(d1 to dN), each data set having N data points. The M spectral data sets or time-domain data sets S1(d1 to dN) to SM(d1 to dN) are accumulated. Correlations between the sets S1(dn) to SM(dn), each set containing the data points of the same ordinal number dn, contained in the M spectral data sets or time-domain data sets S1(d1 to dN) to SM(d1 to dN) are found to thereby find a correlation data set C(c1 to cN) indicating the correlation strengths about the data points of the ordinal numbers. Then, the product of an accumulated or anticipated spectral data set or time-domain data set Sav(d1 to dN) which is obtained by an accumulation operation and which contains N data points and the correlation data set C(c1 to cN) is found.

Another method of processing data in accordance with the present invention starts with performing a step consisting of repeatedly making a measurement while varying at least one measurement parameter in M increments to thereby obtain M data sets S1(d1 to dN) to SM(d1 to dN), each data set containing N data points. Then, correlations of data representing variations anticipated in response to variations in the parameter regarding sets S1(dn) to SM(dn), each set containing data points of the same ordinal number dn, contained in the M data sets S1(d1 to dN) to SM(d1 to dN) are found to thereby find a correlation data set C(c1 to cN) indicating correlation strengths about the data points of the ordinal numbers. Either the product of an accumulated or anticipated data set Sav(d1 to dN) which has N data points and which is obtained by an accumulation operation after correcting effects of variations in the parameter regarding the data sets S1(d1 to dN) to SM(d1 to dN) and the correlation data set C(c1 to cN) or the product of a separately measured data set So(d1 to dN) and the correlation data set C(c1 to cN) is found.

A spectrometer according to the present invention comprises: accumulation means for accumulating M spectral data sets or time-domain data sets S1 (d1 to dN) to SM (d1 to dN) which are obtained by repeating the same measurement M times, each of the data sets having N data points; correlation computing means for finding correlations between sets S1 (dn) to SM(dn), each having data points of the same ordinal number dn, contained in the M spectral data sets or time-domain data sets S1 (d1 to dN) to SM (d1 to dN) to thereby find a correlation data set C (c1 to cN) indicating correlation strengths of the data points of the ordinal numbers; and computing means for finding the product of an accumulated or anticipated spectral data set Sav (d1 to dN) and the correlation data set C(c1 to cN). Consequently, signal and noise can be discriminated from each other more efficiently.

A measuring apparatus according to the present invention comprises: correlation computing means for finding correlations of data representing variations anticipated in response to variations in at least one measurement parameter regarding sets S1 (dn) to SM (dn), each having data points of the same ordinal number dn, which are contained in M data sets S1 (d1 to dN) to SM (d1 to dN), each set having N data points, and which are obtained by repeatedly making a measurement while varying the parameter in M increments to thereby find a correlation data set C (c1 to cN) indicating correlation strengths about the data points of the ordinal numbers; and computing means for finding the product of an accumulated or anticipated data set Sav (d1 to dN) which has N data points and which is obtained by an accumulation operation after correcting effects of variations in the parameter regarding the data sets S1 (d1 to dN) to SM (d1 to dN) and the correlation data set C (c1 to cN) or the product of a separately measured data set So(d1 to dN) and the correlation data set C (c1 to cN). In consequence, noise can be compressed, and the signal-to-noise ratio can be improved greatly.

A method of processing data in accordance with the present invention starts with accumulating M spectral data sets or time-domain data sets S1 (d1 to dN) to SM (d1 to dN) which are obtained by repeating the same measurement M times, each data set having N data points. Correlations between sets S1 (dn) to SM (dn), each containing data points of the same ordinal number dn, which are contained in the M spectral data sets or time-domain data sets S1 (d1 to dN) to SM (d1 to dN) are found to thereby find a con-elation data set C (c1 to cN) indicating correlation strengths of data points of the ordinal numbers. The product of an accumulated or anticipated spectral data set or time-domain data set Sav (d1 to dN) which has N data points and which is obtained by an accumulation operation and the correlation data set C (c1 to cN) is found. Consequently, noise is compressed, and the signal-to-noise ratio can be improved greatly.

Another method of processing data in accordance with the invention starts with performing a step consisting of obtaining M data sets S1 (d1 to dN) to SM (d1 to dN), each data set having N data points, by repeatedly making a measurement while varying at least one parameter in M increments. Correlations between data representing variations anticipated in response to variations in the parameter regarding sets S1 (dn) to SM (dn), each containing data points of the same ordinal number dn, contained in the M data sets S1 (d1 to dN) to SM (d1 to dN) are found to thereby find a correlation data set C (c1 to cN) indicating correlation strengths of the data points of the ordinal numbers. Either the product of an accumulated or anticipated data set Sav (d1 to dN) which has N data points and which is obtained by an accumulation operation after correcting effects of variations of the parameter regarding the data sets S1 (d1 to dN) to SM (d1 to dN) and the correlation data set C (c1 to cN) or the product of a separately measured data set So (d1 to dN) and the correlation data set C (c1 to cN) is found. In consequence, noise can be compressed, and the signal-to-noise ratio can be improved greatly.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

FIGS. 8A and 8B show diagrams illustrating the correlations between an observed phase and the phase of an NMR signal in Embodiment 2;

FIG. 9 is a schematic representation of one example of NMR measurement scheme according to Embodiment 3 of the invention, for observing an NMR signal;

DESCRIPTION OF THE PREFERRED EMBODIMENTS

Although the present invention can be applied to all the fields of spectroscopy, the invention is herein described only in relation to NMR. In the past, plural measurements were made to produce sets of data, and only the results of summation (accumulation) of the sets of data were treated as measurement results. In the present invention, the sets of data produced prior to the summation are noticed, as well as the results of the accumulation. As a result, the sensitivity is improved efficiently.

A great advantage of the present invention is that normal accumulation results are derived simultaneously. Therefore, if the results are unsatisfactory, then what should be done is only to adopt results produced by the conventional method; nothing will be lost compared with the prior art.

Normally, NMR signals are observed as time-domain signals. Such a time-domain signal may be analyzed as it is. A time-domain signal may be Fourier transformed and treated as a frequency-domain signal (known as a spectrum). Furthermore, depending on a method of measurement, a frequency-domain signal may be observed directly. In any case, a signal in the frequency domain or time domain is finally analyzed. The present method can be applied to both time-domain and frequency domain signals. In the following embodiments, it is assumed, for simplicity, that frequency-domain signals are processed.

For the sake of simplicity, in Embodiments 1-6, the simplest one-dimensional NMR measurements are described. However, it is easy to extend the present method to multidimensional NMR spectroscopy by replacing an excitation pulse by a multidimensional NMR measurement. The present invention can also be applied to such multidimensional NMR spectroscopy.

Figure 1:
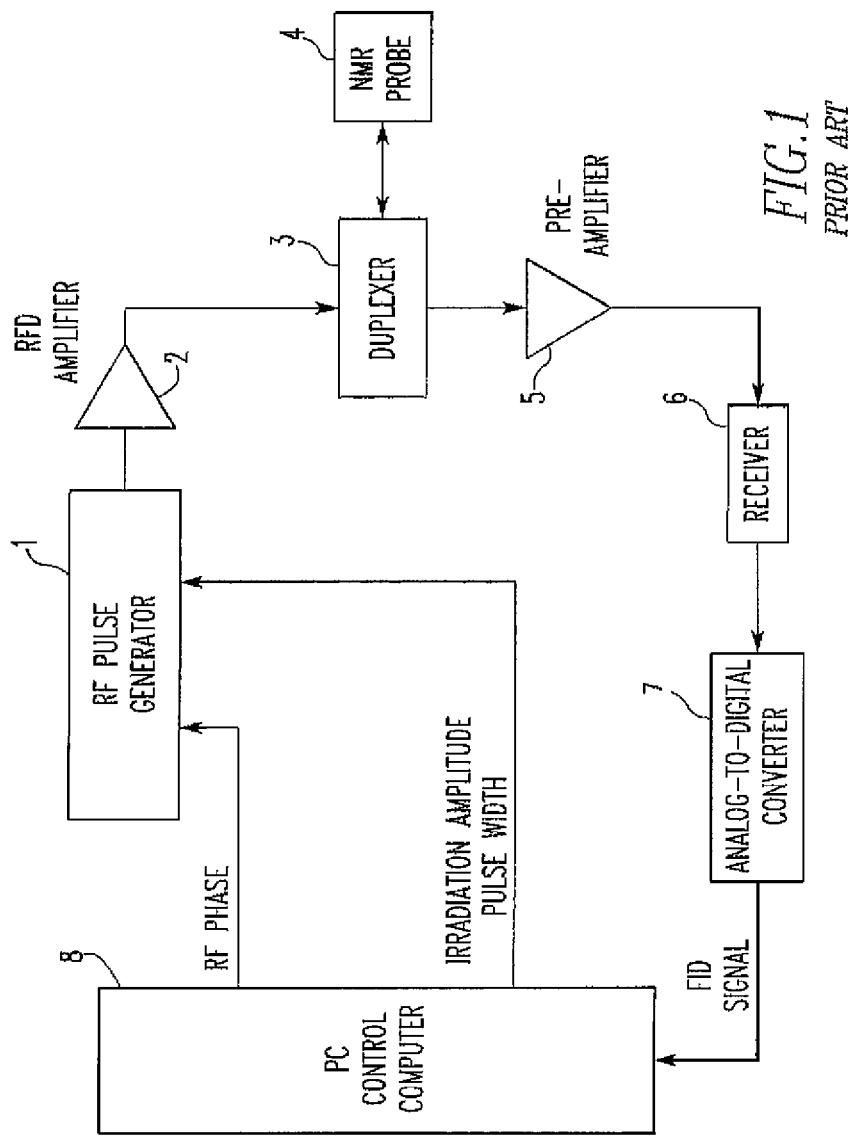
FIG. 1 is a schematic block diagram of a conventional NMR spectrometer.
Figure 2:
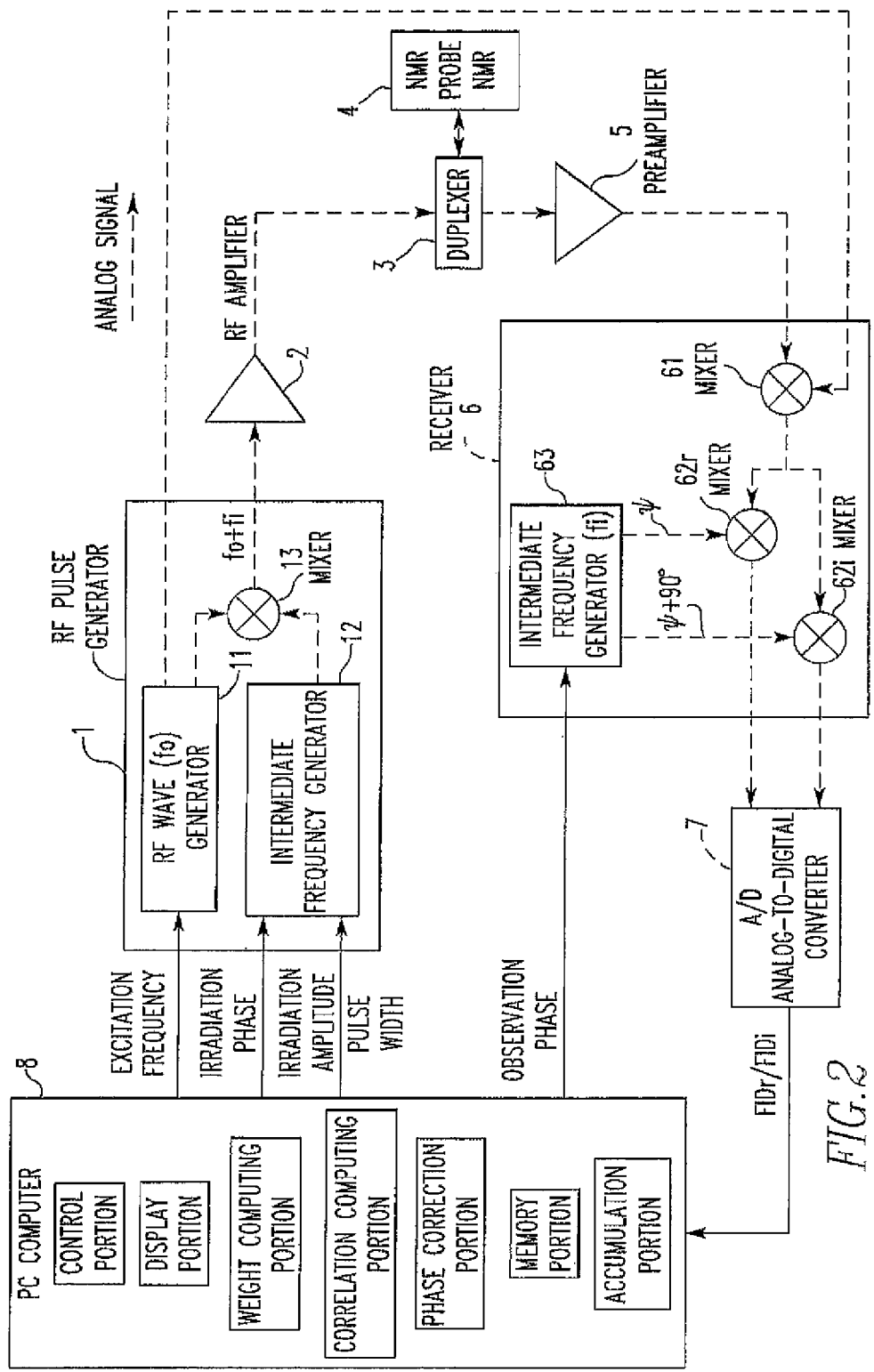
FIG. 2 is a block diagram showing an example of configuration of an NMR spectrometer that can be used in common among various embodiments of the present invention.

FIG. 2 shows one example of structure of an NMR spectrometer that can be used in common among various embodiments (described below) of the invention. The structure of FIG. 2 is based on the conventional structure shown in FIG. 1 but shown in further detail. In FIGS. 1 and 2, like components are indicated by like reference numerals.

Referring to FIG. 2, an RF pulse generator 1 is configured including an RF wave generator 11, an intermediate frequency (IF) generator 12, and a mixer 13. The intermediate frequency generator 12 produces a pulsed-sinusoidal wave of an intermediate frequency fi. The pulsed wave of the intermediate frequency is mixed with an RF wave of a frequency fo generated from the RF wave generator 11 by the mixer 13. As a result, an exciting RF pulse having a frequency of fo+fi (or fo−fi) to excite nuclei under investigation is created. The exciting RF pulse is fed to an NMR probe 4 via an RF amplifier 2 and a duplexer 3. The pulse is applied to a sample under investigation from an irradiation/detection coil (not shown) placed within the NMR probe 4.

After the irradiation with the exciting RF pulse, a feeble NMR signal (free induction decay (FID) signal) generated by the sample is detected by the irradiation/detection coil. The resulting signal is fed to a receiver 6 via the duplexer 3 and a preamplifier 5.

The receiver 6 is configured including a mixer 61 for mixing the NMR signal amplified by the preamplifier 5 and the RF wave of the frequency fo generated by the RF wave generator 2 to thereby convert the NMR signal into a signal of an intermediate frequency, two demodulation mixers 62r and 62i to which the output from the mixer 61 is supplied, and an intermediate frequency generator 63 for producing intermediate frequencies which have the same frequency fi but are 90° out-of-phase. The intermediate frequencies are supplied as reference signals to the demodulation mixers 62r and 62i.

The demodulation mixers 62r and 62i operate as 90° out-of-phase 2-channel demodulators by employing the 90° out-of-phase reference waves. Free induction decay signals of a pair, FIDr and FIDi, in the audio frequency region obtained by demodulation effected by the 2-channel demodulators are converted into digital signals by an A/D converter 7 and then fed to a control computer 8, where the signals are stored in its storage portion.

A signal for specifying an excitation frequency corresponding to the nuclei under investigation is supplied to the RF wave generator 11 from the control computer 8. A signal for specifying the phase φ of the irradiation pulse and signals for specifying the amplitude and pulse width of the exciting RF pulse are supplied to the intermediate frequency generator 12 from the computer 8. A signal for specifying the phase φ to be observed is supplied to the intermediate frequency generator 63 of the receiver 6 from the computer 8.

The control computer 8 has a control portion for controlling the measurement conditions as described previously. In addition, the computer 8 has a Fourier transform processing portion for obtaining an NMR spectral signal in the frequency domain by subjecting the FID signal accepted in the time domain into a complex Fourier transform process, a phase correction portion for phase correcting the NMR spectral signal as necessary, a display portion for displaying an NMR spectrum and a control window, an accumulation portion for accumulating FID signals, a correlation computing portion, and a weight computing portion. The computing portions are closely related to the present invention.

In the above-described structure, if hydrogen nuclei are specified, for example, as the observed nuclei, the control computer 8 provides control such that the RF wave generator 11 produces the frequency fo that makes the frequency (fo+fi) equal to the resonance frequency of the hydrogen nuclei. Also, the control computer appropriately specifies the pulse width and pulse amplitude of the exciting RF pulse. Furthermore, the computer specifies the phase φ of the RF wave contained in the exciting RF pulse according to the need. Consequently, the RF pulse generator 1 produces exciting RF pulses having desired pulse width and pulse width and a desired RF phase regarding the desired nuclei under observation. The pulses are applied to the sample within the NMR probe 4 via the duplexer 3.

The NMR signal which was detected and amplified by the preamplifier 5 after the irradiation with the exciting RF pulse is mixed with the RF wave of the frequency fo generated from the RF wave generator 2 by the mixer 61 to convert the NMR signal into an intermediate frequency. The signal is then supplied to the 2-channel demodulators 62r and 62i which are 90° out-of-phase. The method of demodulation using the 90° out-of-phase 2-channel demodulators is known as quadrature detection. One of FID signals obtained by demodulation from the channels is treated as a real-part component, while the other is treated as an imaginary-part component. A pair of NMR spectral data, or a real spectrum and an imaginary spectrum, can be obtained by subjecting the FID signals to complex Fourier transform.

The real spectral data and imaginary spectral data are respectively denoted by r and i. The phase at each point forming a spectrum can be found from arctan (i/r). Conversely, using this relationship, a phase correction at any arbitrary spectral position can be made.

The control computer 8 can give appropriate instructions to set the phase φ of the demodulators 62r and 62i relative to the irradiation phase φ as the observation phase according to the need.

Embodiments of the invention implemented using the NMR spectrometer configured as described so far are described below.

Embodiment 1

Figure 3:
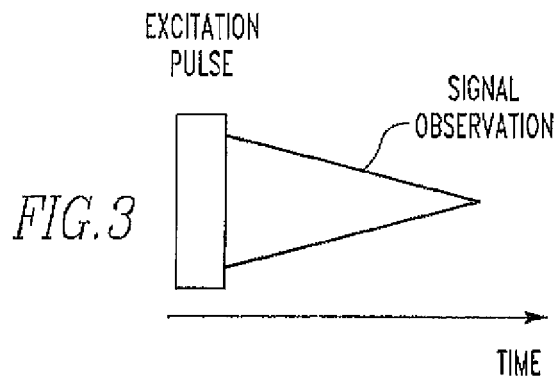
FIG. 3 is a schematic representation of one example of NMR measurement scheme for observing an NMR signal.

FIG. 3 shows the simplest measurement sequence for observing an NMR signal. Magnetization of the nuclei under observation is excited by an excitation pulse and observed as an NMR signal (FID signal) in the time domain. The signal is Fourier transformed. As a result, a frequency-domain NMR signal, i.e., an NMR spectrum, is obtained.

Figure 4:
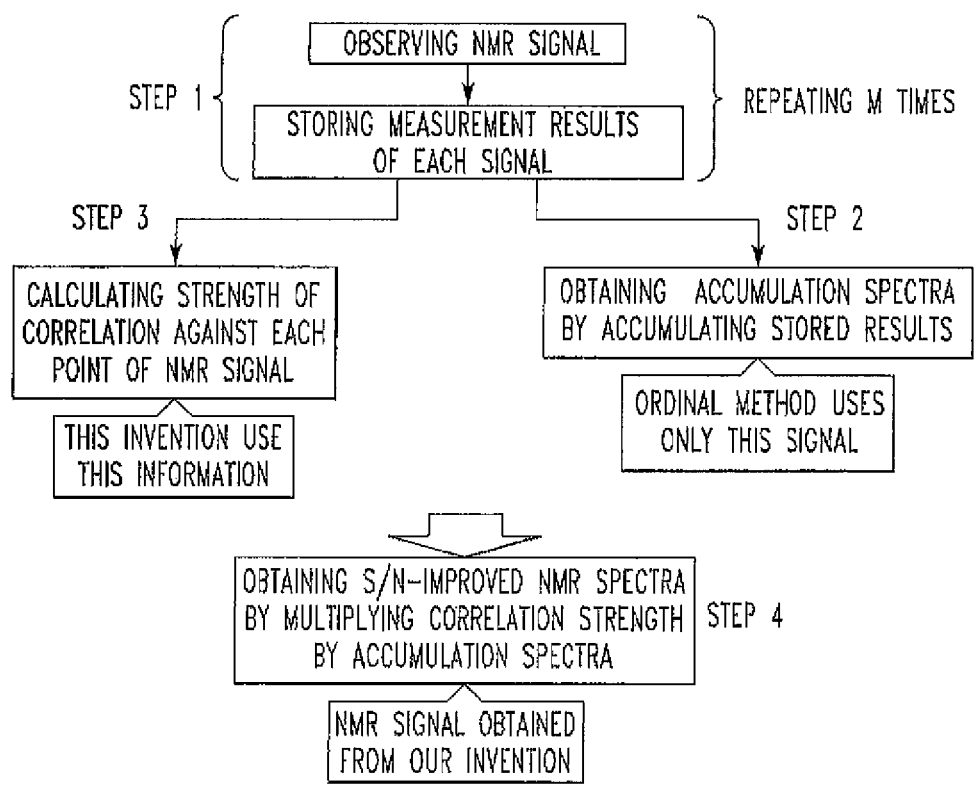
FIG. 4 is a flowchart illustrating a sequence of operations performed in a first embodiment of the invention.

The present embodiment is a technique for measuring the correlations between measurements of the intensity (or phase) at each point of an NMR signal when the same measurement is repeated. The flow of the sequence of operations in the present embodiment is illustrated in FIG. 4. In the flow of FIG. 4, the first step 1 is a step for a repetitive measurement. An NMR signal is measured using an observation sequence shown in FIG. 3 and Fourier transformed to obtain an NMR spectrum, which is stored in the storage portion. The process described so far is repeated M times.

When M measurements performed under the same conditions are completed, it follows that M spectral data sets S1 (d1 to dN) to SM (d1 to dN) are stored in the storage portion of the control computer 8 as shown in (a) of FIG. 5, N being the number of data points in each NMR spectrum.

Figure 5A:
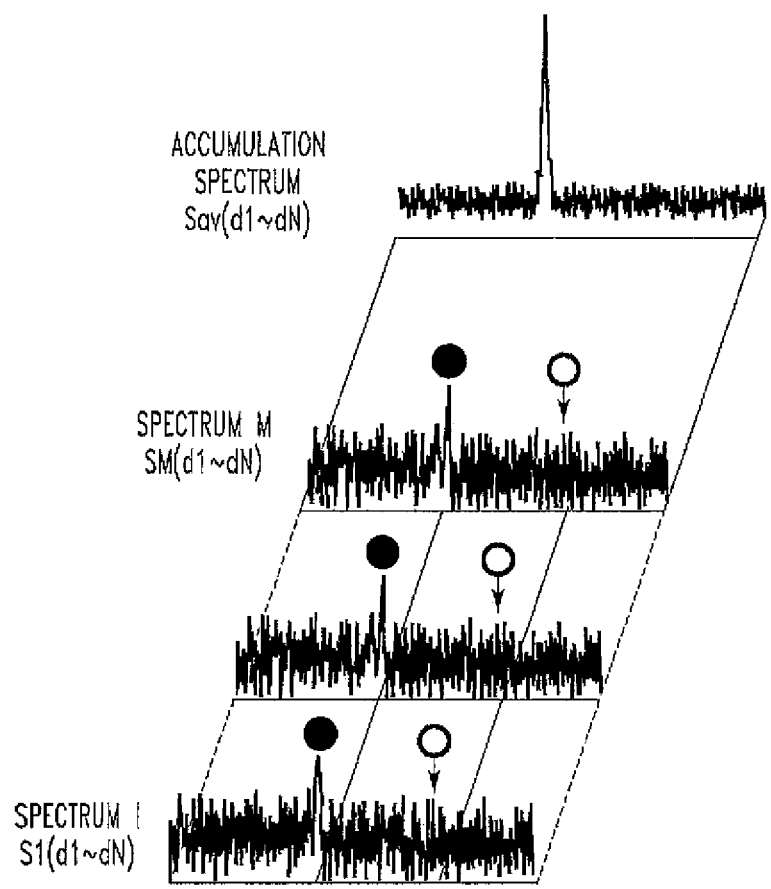
FIGS. 5A to 5E are diagrams illustrating NMR spectra, an NMR accumulation spectrum, and two types of correlation data obtained during a measurement process according to the first embodiment.

Step 2 is an accumulation operation consisting of simply adding up the M stored NMR spectral data sets. As a result, an accumulated spectral data set Sav (d1 to dN) as shown in FIG. 5A is obtained. In the prior art, the NMR measurement would end at this point. In the present invention, steps 3 and 4 described next are added.

That is, step 3 is a correlation computing step for calculating the correlation strengths between data sets (e.g., values of correlation coefficient r and their absolute values) from the degrees of variations of data regarding sets (S1 (d1) to SM (d1), (S1 (d2) to SM (d2), (S1 (d3) to SM (d3), . . . , (S1 (dn) to SM (dN)), each set consisting of data of the same ordinal number, of NMR spectral data sets S1 (d1 to dN) to SM (d1 to dN) to thereby obtain a correlation data set C (c1 to cN).

Figures 5B, 5C:
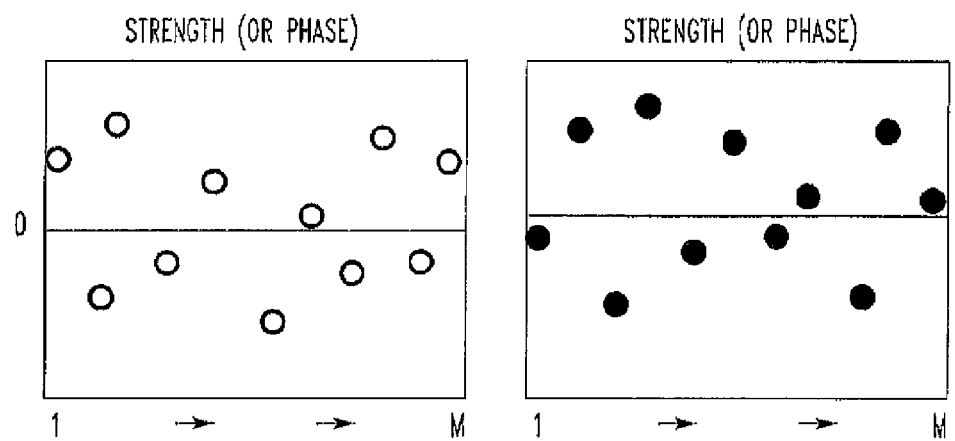

The correlation calculation is described by referring to FIGS. 5B to 5C. NMR spectral data sets S1 (d1 to dN) to SM (d1 to dN) are shown in FIG. 5A. Each black circle indicates a position (ordinal number) at which an NMR signal exists, while each white circle indicates a position (ordinal number) at which only noise is present. M data sets indicated by the black circles and M data sets indicated by the white circles are plotted in the charts of FIGS. 5B and 5C, where spectral number (1 to M) is plotted on the horizontal axis and spectral intensity (or phase) is on the vertical axis. As can be seen from the charts of FIG. 5B and FIG. 5C, the sets of noise data indicated by the white circles are distributed in the up-down direction about the level of intensity zero. The sets of NMR signals (indicated by the black circles) on which noise is superimposed are distributed in the up-down direction about a level shifted upward from the level of the intensity zero by an amount corresponding to the NMR signal intensity.

Figures 5D, 5E:
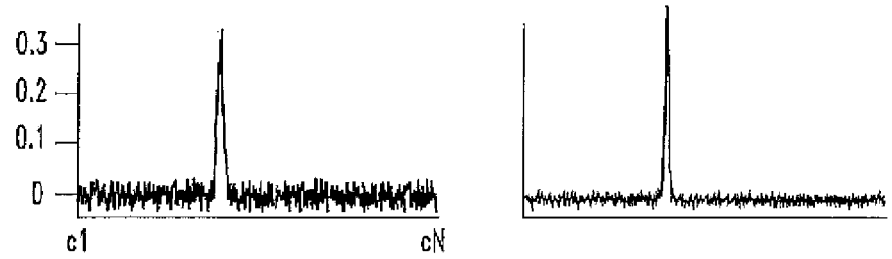

That is, the black circles indicating signal intensities or phases are distributed in such a way that they are concentrated always near a certain value if noise is superimposed on the signal because the NMR signal exhibits the same value at all times. On the other hand, on the white circles indicating only noise, signal intensities or phases are distributed randomly about the zero level. By calculating correlations about the distribution always near the certain value based on the above-described difference, the correlation data set C (c1 to cN) indicating the correlation strengths regarding NMR signals at each position of NMR spectra can be found as shown in FIG. 5D.

The final step 4 of the procedure of FIG. 4 is a step for computing weights, i.e., multiplies an accumulation spectral data set Sav (d1 to dN) by the correlation data set C (c1 to cN). That is, the accumulation spectral data set Sav (d1 to dN) found in step 2 and shown in FIG. 5A is multiplied by the correlation data set C (c1 to cN) shown in FIG. 5D while aligning the positions. As a result, data about noise portions having small correlation coefficients are greatly attenuated or compressed, while data about locations where an NMR signal is present and correlation coefficients are large are not attenuated greatly. As a consequence, as shown in FIG. 5E, in the accumulation spectrum, noise portions are compressed.

In the above description, an example is given in which correlations about intensities are found. In this example, data about only real spectra need to be used. In order to find the correlations about phases, data i about imaginary spectra are used in addition to data r about real spectra, and the phase at each point of a spectrum is found from arctan (i/r) as described previously. Let p1 to pN be the phase values at N points making up each spectrum. Regarding the M spectral data sets S1 (d1 to dN) to SM (d1 to dN), phase data sets S1 (p1 to pN) to SM (p1 to pN) are found from real and imaginary data.

Based on the found phase data sets S1 (p1 to pN) to SM to pN), the correlation strengths between data sets (e.g., values of correlation coefficient r and their absolute values) are computed from the degrees of variation of data concerning sets S1 (p1) to SM (p1), S1 (p2) to SM (p2), S1 (p3) to SM (p3), S1 (pN) to SM (pN), each set consisting of data of the same ordinal number, to obtain the correlation data set C (c1 to cN), in the same way as when the correlations of the intensities are found as described previously.

Where the correlations about the phases are found in this way, data about locations where an NMR signal is present are distributed in a narrow range about the phase 0° always exhibited by the NMR signal. Data about locations where only noise is present are randomly distributed over a wide range from 0° to 360°. The correlation data set C (c1 to cN) can be obtained based on phases by calculating correlations in such a way that the correlation coefficient varies according to the different distributions.

As mentioned previously, in the case of NMR spectroscopy, an NMR signal emanating from an excited magnetization is normally derived as time-domain FID data, which are Fourier transformed to obtain NMR spectral data. In the above description, spectral data obtained by a Fourier transform are multiplied by correlation strengths. In practice, a spectrum having a greatly improved signal-to-noise ratio can be produced by finding correlations about time-domain data not yet subjected to Fourier transform, multiplying the found correlation strengths by accumulation data obtained by accumulating time-domain data, and Fourier transforming the resulting products. Obviously, an accumulation spectrum as produced in the past can be obtained by Fourier transforming the accumulation data of time-domain data.

The present embodiment can be applied to an ESR spectrometer, an electromagnetic spectrometer employing X-rays, ultraviolet rays, visible light, infrared radiation, microwaves, or radio waves, a mass spectrometer, an instrument utilizing a charged-particle beam (including an electron microscope), and an imaging apparatus employing any of such instruments, as well as to an NMR spectrometer.

A great advantage of the present invention is that normal NMR spectra owing to accumulation (accumulation data) are derived simultaneously. If NMR spectra obtained by the inventive processing are unsatisfactory, then what should be done is only to adopt NMR spectra produced by an accumulation method; the measurer will lose nothing compared with the prior art. A memory space for storing currently observed NMR signals which would be normally discarded is necessary but this presents no practical problems at all because modern equipment has a memory of large storage capacity.

Measurement data which are successively stored in memory to find correlations are not always derived from the result of a single measurement. In many cases, it is desired to perform the inventive processing consisting of performing a certain number of accumulation steps on measurement data, storing the results in memory, finding correlations about the stored results, and multiplying the found correlations by accumulation data in order to obtain desired signals or erase artifacts.

Embodiment 2

The present embodiment is a technique for measuring the correlation between the phase observed in an NMR spectrometer and the phase at each point of a measured NMR signal.

Figure 6:
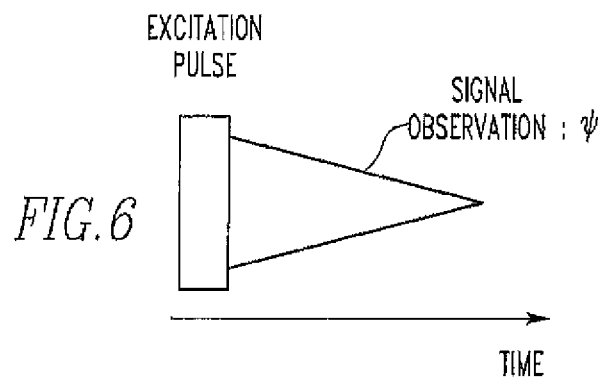
FIG. 6 is a schematic representation of one example of NMR measurement scheme according to Embodiment 2 of the invention, for observing an NMR signal.

In the present embodiment, a sequence of measurements is performed in which only the phase φ of the observed signal is varied. The simplest measurement is shown in FIG. 6. In particular, when measurements are made by the procedure of FIG. 4 using the NMR spectrometer of FIG. 2, the observed phase φ is varied in step 1 whenever a measurement is performed. In this way, M measurements are carried out in turn. NMR spectral data sets S1 (d1 to dN) to SM (d1 to dN) are stored in the storage portion together with the corresponding observed phase φ.

Figure 7:
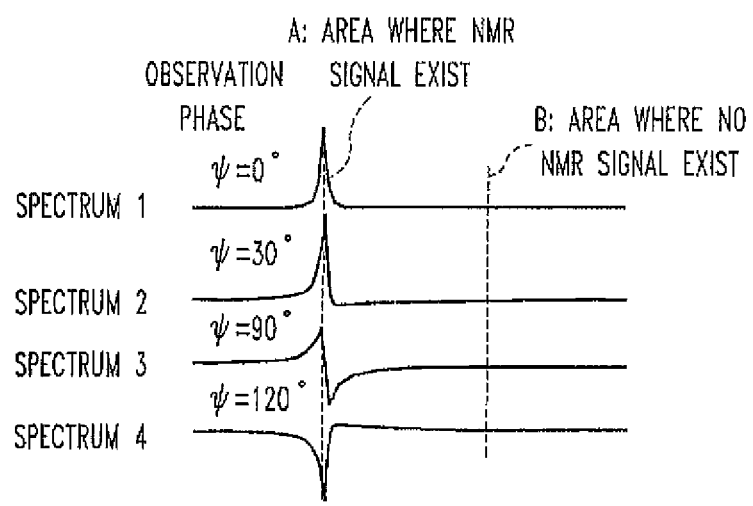
FIG. 7 is a conceptual diagram showing how observed NMR signals vary in response to variation of an observation phase.

It is anticipated that the observed phase of the NMR signal will vary in synchronism with the observed phase φ of the signal. On the other hand, the phase of noise is independent of the observed phase φ of the signal. FIG. 7 conceptually illustrates how actually observed signals vary when the observation phase changes. It is assumed that a pure NMR signal exists at point A. When the phase observed by an NMR signal is 0°, a pure NMR signal assumes a pure absorption waveform. When the observation phase is 90°, the signal assumes a dispersion waveform. At other phases, the signal assumes waveforms between the absorption and dispersion waveforms. In this way, the pure NMR signal varies according to the observation phase. In FIG. 7, only real-part spectra r are shown in a conventional manner. As described previously, imaginary-part spectra i are also present in practice. The phase at each point of an NMR spectrum is defined as arctan (i/r).

On the other hand, at locations (such as point B) where there is no true NMR signal, only noise is observed. If the phase of the data observed at point B is found using arctan (i/r), random phase is shown because noise shows no correlation with the observation phase of the NMR spectrometer.

In the present embodiment, the observation phase is varied whenever a measurement is made. Therefore, the observation phase of the NMR signal varies accordingly. Consequently, during an accumulation operation of step 2 of the procedure shown in FIG. 4, if NMR spectra obtained by measurements are simply accumulated, the NMR signals will be averaged and attenuated. Hence, it is impossible to enjoy the benefit of the accumulation technique. Accordingly, during the accumulation step (step 2) of the procedure of FIG. 4, an accumulation spectral data set Sav (d1 to dN) equivalent to data obtained by the ordinary accumulation method can be obtained by making a phase correction in such a way that the phases of all NMR spectra obtained by measurements are kept at 0° in spite of variation of the observation phase and summing up the corrected NMR spectra.

The correlation between the observation phase and the phase of an NMR signal is shown in FIG. 8. At position A, a correlation of tilt 1 appears. On the other hand, at position B, there is no correlation. Accordingly, the correlation strength is higher at the position A and lower at the position B. The correlation strengths at points of NMR spectra are derived by performing an operation for computing the correlations in step 3.

More specifically, as already described in Embodiment 1, M spectral data sets S1 (d1 to dN) to SM (d1 to dN) are measured while varying the observation phase ϕ in M increments. With respect to these M spectral data sets, the correlation data set C (c1 to cN) is derived by obtaining phase data sets S1 (p1 to pN) to SM (p1 to pN) from real data and imaginary data and making decisions as to whether a correlation of tilt 1 appears between variations in the observation phase and phase data regarding sets (S1 (p1) to SM (p1), (S1 (p2) to SM (p2), (S1 (p3) to SM (p3), . . . , (S1 (pN) to SM (pN)), each set being a collection of data of the same ordinal number, based on the found phase data sets S1 (p1 to pN) to SM (p1 to pN). That is, a processing step for determining the correlation strength is performed. The subsequent step 4 is the same as that of Embodiment 1. In step 2, variations in the observation phase are corrected and then spectral data are accumulated to produce the accumulation NMR spectral data set Sav (d1 to dN). The NMR spectral data set Sav is multiplied, or weighted, by the correlation data set C (c1 to cN) found in step 3. Consequently, an NMR spectrum with good S/N can be derived.

This is expressed more generally. A measurement is repeated while varying at least one measurement parameter in M increments, thus yielding M data sets S1 (d1 to dN) to SM (d1 to dN). Each of the data sets has N data points. The correlations of the sets of data points, each set containing data points of the same ordinal number, contained in the M data sets S1 (d1 to dN) to SM (d1 to dN) with data representing variations anticipated in response to variations in the parameter are found. The correlation data set C (c1 to cN) indicating correlation strengths about the data points of the ordinal numbers is found. This constitutes a correlation computing means. The product of the accumulation data set Sav (d1 to dN) which has N data points and which is obtained by accumulating the data sets S1 (d1 to dN) to SM (d1 to dN) after correcting effects of variations in the parameter and the correction data set C (c1 to cN) or the product of a separately measured data set So (d1 to dN) and the correlation data set C (c1 to cN) is found. This constitutes a computing means.

The present embodiment can be applied to NMR spectrometers. Besides, the present embodiment can be applied to any apparatus that makes a measurement and produces measurement results involving variations which can be forecasted or detected due to variations in the parameter (such as an ESR spectrometer, an electromagnetic spectrometer employing X-rays, ultraviolet rays, visible light, infrared radiation, microwaves, or radio waves, a mass spectrometer, an instrument utilizing a charged-particle beam (including an electron microscope), or an imaging apparatus employing any of such instruments).

Embodiment 3

The present embodiment is a technique for measuring the correlations between an excitation phase used in an NMR spectrometer and the phases at various points in the measured NMR signal.

In Embodiment 2, the observation phase ϕ is varied. In the present embodiment, a sequence of measurements is performed while varying only the phase of an exciting RF pulse. The simplest measurement sequence is illustrated in FIG. 9. In particular, when measurements are performed by the procedure of FIG. 4 using the NMR spectrometer shown in FIG. 2, the irradiation phase (excitation phase) ϕ of which an indication is provided to the intermediate frequency generator 12 in step 1 is varied whenever a measurement is made. NMR signals for each excitation phase are stored in the storage portion.

The operation of the present embodiment closely resembles the operation of Embodiment 2. It is anticipated that the measured phase of the NMR signal will vary in response to the excitation phase ϕ. On the other hand, noise is independent of the excitation phase ϕ. Accordingly, the present embodiment can be implemented by finding the strength of the correlation of the phase of the NMR signal measured under the condition of the excitation phase ϕ with a straight line of tilt 1 in step 3.

Figure 10A:
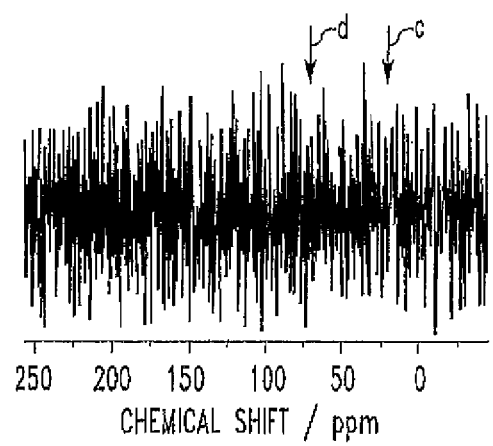
FIGS. 10A to 10F show diagrams illustrating an NMR spectrum, an NMR accumulation spectrum, correlation plots, correlation data, and the results of the product of the accumulation spectrum and the correlation data, all obtained by a measurement process according to a third embodiment of the invention.

An example of actual measurement is given next. FIG. 10A shows one example of NMR signal obtained by each measurement prior to an accumulation operation. The signal was almost entirely buried in noise. It was difficult to extract the NMR signal. In step 1, the measurement was repeated 1800 times. That is, the excitation phase 360° of the NMR spectrometer was divided into 1800 parts. The measurements were performed while shifting the excitation phase of the NMR spectrometer in increments of 360°/1800. As a result, 1800 NMR spectral data sets (S1 (d1 to d1024) to S1800 (d1 to d1024), each data set having 1024 data points, were stored in the storage portion.

Figure 10B:
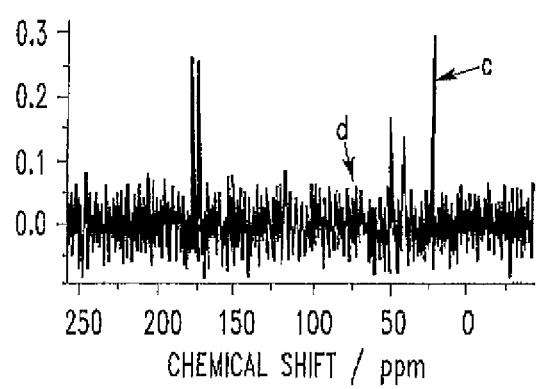
Figure 10C:
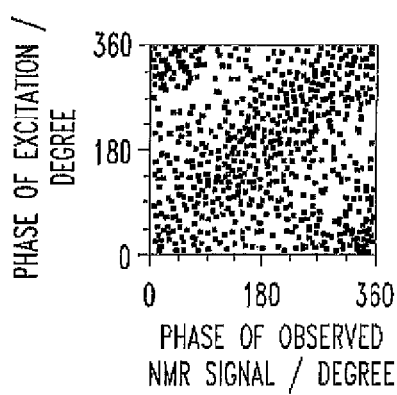
Figure 10D:
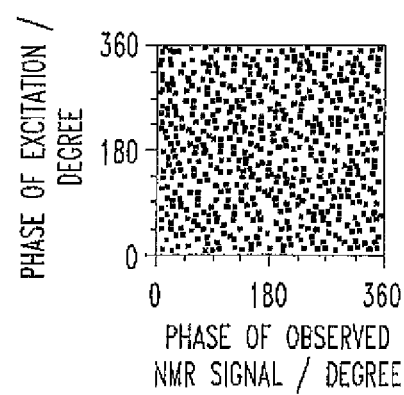
Figure 10E:
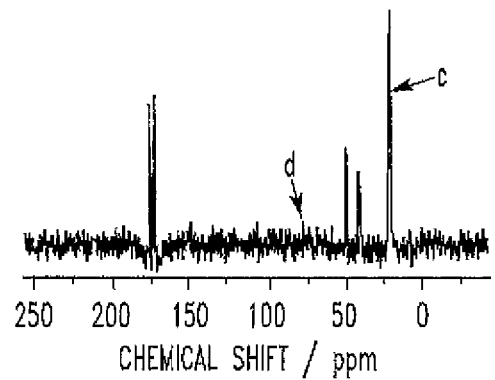

An accumulation spectrum produced by accumulating the 1800 spectra in step 2 is shown in FIG. 10E. Prior to the accumulation operation, the NMR spectra were phase corrected for variations in the NMR spectra incurred by shifting the excitation phase in increments of 0.5° and the phases were aligned to 0°, in exactly the same way as in the operation of Embodiment 2 for correcting the phases and performing the accumulation operation. A spectrum identical with accumulation NMR spectra derived by the conventional accumulation technique was obtained. It can be seen from FIG. 10A that some signals which could not be noticed at all in a single measurement can be observed.

The correlative relationship between the phase at each point of NMR spectra obtained by the measurements and the excitation phase is described. As an example, correlation plots of the positions of points c and d which are typical two points in those NMR spectra are shown in FIGS. 10C and 10D. In this case, 1800 data points of ordinal numbers corresponding to the points c and d in the 1800 NMR spectral data sets obtained by 1800 measurements are plotted in each chart.

From the correlation plot (FIG. 10C) of data at the position of the point c (of FIG. 10A) where it is considered that there is undoubtedly an NMR signal from the result of the accumulation, a correlation of tilt 1 (correlation coefficient of almost 1) is clearly seen. On the other hand, from the correlation plot (FIG. 10D) of data about the position of the point d where it is considered that there is no signal but only noise exists, it can be seen that there is no correlation (correlation coefficient of nearly 0) between the phase of the spectrum obtained by a measurement and the excitation phase. In step 3, the correlation data set C (c1 to c1024) is obtained by finding the strength of correlation with the straight line of tilt 1 at each point.

An example of actual calculation of correlations is described below. Measurements are made while shifting the excitation phase in 1800 increments to thereby obtain 1800 spectral data sets S1 (d1 to d1024) to S1800 (d1 to d1024), in the same way as in Embodiment 2. With respect to these spectral data sets, phase data sets S1 (p1 to p1024) to SM (p1 to p1024) are found from real data and imaginary data. Based on the found phase data sets S1 (p1 to p1024) to S1800 (p1 to p1024), the strengths of correlative relationships between the variation in the excitation phase and the phase data are found to know whether or not there is a correlation of tilt 1 between them regarding sets S1 (p1) to S1800 (p1), S1 (p2) to S1800 (p2), S1 (p3) to S1800 (p3), S1 (p1024) to S1800 (p1024), each set being a collection of data of the same ordinal number. That is, a process for computing the correlations is performed. Thus, a correlation data set C (c1 to c1024) is obtained.

One example of mathematical formula used to implement the calculations of the correlations is given in Eq. (1).

$$\rho_i = \frac{\langle p_{ij}\phi_j\rangle - \langle p_{ij}\rangle\langle\phi_j\rangle}{\sqrt{(\langle p_{ij}^2\rangle - \langle p_{ij}\rangle^2)(\langle\phi_j^2\rangle - \langle\phi_j\rangle^2)}} \quad (1)$$

where $p_{ij}$ indicate arbitrary phase data within the phase data sets S1 (p1 to p1024) to S1800 (p1 to p1024), where i is an integer assuming a value from 0 to 1024-1 and is an ordinal number (index) indicating a point in a spectrum and j is an integer assuming a value from 0 to 1800-1 and is an ordinal number indicating the number of repetition when the measurement was repeated, $\phi_j$ indicates the excitation phase when the jth measurement was made, and $\rho_i$ indicates a correlation (correlation coefficient) of the ith point in the spectrum. Each arithmetic operation indicated by < > indicates an average taken over various values of j.

In FIG. 10B, 1024 points of the correlation data set C (c1 to c1024) obtained by such correlation computation are plotted. The vertical axis indicates the correlation strength. It can be seen that the correlation strength is very large in locations where there would be a signal and the strength is quite small in locations where there would be no signal.

Figure 10F:
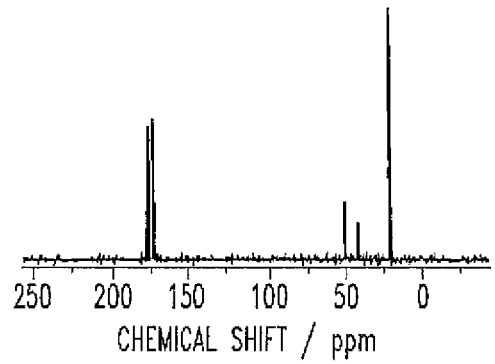

The NMR spectra are phase corrected for variations in the spectra caused by variations in the excitation phase and the phases of the NMR spectra are aligned to 0°. The spectra are accumulated to produce the accumulation NMR spectrum shown in FIG. 10E. The accumulation NMR spectrum is multiplied by weight coefficients (one kind of window function) for NMR spectra, the weight coefficients consisting of the correlation data shown in FIG. 10B. The resulting spectrum is shown in FIG. 10F. Compared with the accumulation NMR spectrum of FIG. 10E, noise is clearly compressed and the signal-to-noise ratio of the NMR spectrum (FIG. 10F) is improved. It can be seen that noise and signal have been clearly discriminated from each other.

The present embodiment can be applied to an ESR spectrometer, an electromagnetic spectrometer employing X-rays, ultraviolet rays, visible light, infrared radiation, microwaves, or radio waves, a mass spectrometer, an instrument utilizing a charged-particle beam (including an electron microscope), or an imaging apparatus employing any of such instruments, as well as to an NMR spectrometer, in the same way as in Embodiment 2.

The step for multiplying an ordinary accumulation spectrum by weight coefficients (or one kind of window function) for NMR spectra is performed after acquisition of the ordinary accumulation spectrum in the same way as in Embodiments 1 and 2. Therefore, a person who favors a normal method may be allowed to make a choice to deactivate this function. Therefore, the present invention has the quite excellent advantage that conventional spectra data are not destroyed.

Embodiment 4

The present embodiment is a technique for measuring the correlations between the excitation strength for an NMR signal and the intensities at various points of the measured NMR signal. In particular, when measurements are made by the procedure of FIG. 4 using the NMR spectrometer of FIG. 2, NMR spectra are measured while varying the intensity of the excitation pulse by varying the irradiation amplitude (excitation intensity) of which an indication is provided to the intermediate frequency generator 12 whenever a measurement is made in step 1. NMR spectra produced in response to each excitation intensity are stored in the storage portion.

When the intensity of the excitation pulse is varied while maintaining constant the pulse width, the flip angle by which the observed magnetization is tilted varies. In normal measurements, a 90°-angle bringing about a flip angle of 90° is used. The flip angle and the intensity of the NMR signal have such a correspondence relation that they increase along a sinusoidal curve up to 90°, beyond which they decrease along the sinusoidal curve in a reverse manner.

The accumulation operation performed in step 2 to obtain the accumulation spectrum is done after correcting the intensities obtained all at a flip angle of 90° based on the correspondence relationship for each NMR spectrum according to variations in the intensity of each NMR spectrum caused by variations of the flip angle and aligning all the flip angles in the measurements to 90°, in the same way as in the phase correction and accumulation described in Embodiments 2 and 3. An accumulation spectrum identical with accumulation NMR spectra derived by the conventional accumulation method can be derived.

In step 3, the correlation data set C (c1 to cN) is obtained by calculating the correlation strengths (such as values of correlation coefficient r and their absolute values) using the correlation between the flip angle and the intensity of each NMR signal. The correlation data set is multiplied by the accumulation spectrum found in step 2 to thereby give rise to an NMR spectrum with improved S/N.

In the present embodiment, the excitation intensity is varied to vary the flip angle. Alternatively, the pulse width may be varied instead of the excitation intensity because the flip angle can also be varied by varying the pulse width.

Embodiment 5

The present embodiment is a technique for measuring the correlation between a center frequency used when an NMR signal is observed and the position at which the measured NMR signal actually appears.

In particular, in the NMR spectrometer of FIG. 2, the oscillation frequency of the intermediate frequency generator 63 is made controllable by the control computer 8. NMR measurements are made by the procedure of FIG. 4 while varying the center frequency at which the resulting NMR signal is observed by varying the intermediate frequency (observation frequency) of which an indication is provided to the intermediate frequency generator 63 from the control computer 8 whenever a measurement is performed in step 1. The NMR signal is stored in the storage portion together with each center frequency. By varying the center frequency at which an observation is made is varied in this way, the position (frequency) at which an NMR signal appears varies in synchronism with the set center frequency.

The accumulation operation performed in step 2 to obtain the accumulation spectrum is done after correcting each NMR spectrum for frequency variations caused by the variation in the center frequency for observation and making all the NMR spectra equivalent to NMR spectra derived under the same center frequency for observation, in the same way as in Embodiments 2, 3, and 4. An accumulation spectrum identical with accumulation NMR spectra derived by the conventional accumulation method can be derived.

In step 3, the correlation data set C (c1 to CN) is obtained by calculating the correlation strengths (such as correlation coefficients r and their absolute values) based on the correspondence relationship between the position at which the NMR signal appears and the center frequency. An NMR spectrum with improved S/N is produced by multiplying the accumulation spectrum found in step 2 by the correlation data set.

Embodiment 6

The present invention can be applied to the case where an NMR signal is observed indirectly, as well as to the case where an NMR signal is observed directly. Even in indirect measurements, the aforementioned correlation parameters can be used as it is.

In Embodiments 1-5, techniques for directly observing NMR signals have been described. In the present embodiment, the present invention is applied to a technique in which an indirect measurement is made. Specifically, it is conceivable that the invention will be applied to an indirect observation axis used in multidimensional NMR spectroscopy typified by two-dimensional NMR spectroscopy.

Multidimensional NMR spectroscopy has plural time axes. That is, an NMR signal is stated as a signal intensity relative to plural time variables. In many cases, one of the time variables is a time variable with which an NMR signal is directly observed in real time. This is known as a direct observation axis. Embodiments 1-5 can be applied to an NMR signal having this time variable (or a frequency variable obtained by Fourier transforming a signal indicating the time variable).

On the other hand, there is an indirect measurement axis which makes it possible to obtain an NMR signal by performing a sequence of NMR measurements while varying a time variable without directly observing timewise variations of the NMR signal directly on a real-time basis. The present embodiment is applied to this indirect measurement axis. The techniques described in Embodiments 1-5 are also applied to the indirect measurement axis.

Figure 11:
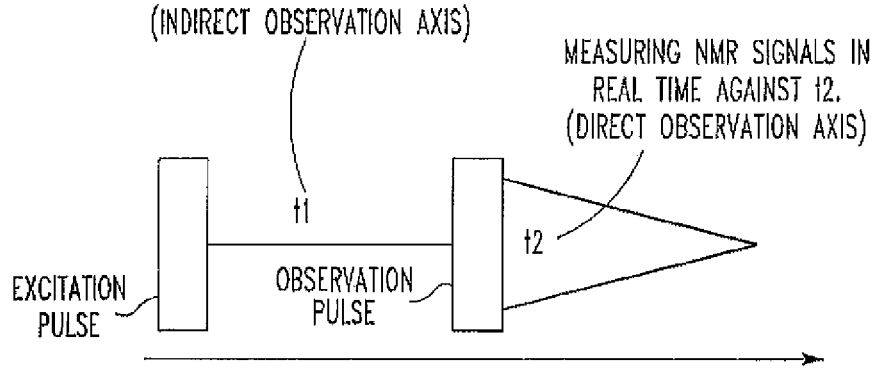
FIG. 11 is a schematic representation of one example of two-dimensional measurement according to Embodiment 3, for observing an NMR signal.

One example of two-dimensional measurement using two time axes, t1 and t2, is shown in FIG. 11 as a specific example of Embodiment 6. In this case, the direct observation axis is t2. Variations in an NMR signal occurring when the variable t2 varies are directly observed on a real time basis. The techniques of the above Embodiments 1-5 can be directly applied to this time axis.

On the other hand, variations in an NMR signal relative to the time t1 can be indirectly observed by performing a sequence of measurements while varying t1. Measurements having plural time axes in this way are known as multidimensional measurements. In this example, there are two variables, i.e., one direct observation axis and one indirect observation axis and, therefore, the measurements are two-dimensional measurements. The method described herein can be directly extended to n-dimensional measurements.

The present invention can be applied to NMR spectroscopy using an indirect observation axis by repeating a measurement with the same t1 and storing the results of the measurements in the storage portion in the case of Embodiment 1. Where the observation phase is varied (corresponding to Embodiment 2), the application of the invention to the NMR spectroscopy can be accomplished by varying the phase of an observation pulse (see FIG. 11) which is known as a read pulse and which is applied immediately after the end of the time t1. Where the phase of the excitation pulse is varied (corresponding to Embodiment 3), the application of the invention to the NMR spectroscopy can be accomplished by varying the phase of an excitation pulse (see FIG. 11) applied immediately before the start of the time t1.

Where the excitation intensity is varied (corresponding to Embodiment 4), the application of the invention to the aforementioned NMR spectroscopy can be accomplished by varying the intensity of the excitation pulse applied immediately prior to the start of the time t1. Where the measurement frequency is varied in Embodiment 5, the application can be accomplished by varying the frequency during the time t1. An equivalent effect can be produced by varying the phase of the read pulse in proportion to the time t1 without varying the frequency during the time t1.

Slice spectra (anticipated spectra) can be extracted by slicing a multidimensional NMR spectrum. The S/N of each extracted slice spectrum can be improved dramatically by multiplying the spectrum by a window function obtained by arranging and plotting data points indicating correlation strengths in accordance with the present invention, for example, as shown in FIG. 10E.

Accordingly, a graphical plot as shown in FIG. 10E is generated by arranging and plotting data points indicating correlation strengths in accordance with the present invention. The graphical plot can be applied to accumulated spectral data or time-domain data. Besides, the graphical plot can be similarly applied to the case where sliced spectra anticipated or forecasted from a multidimensional NMR spectrum are obtained.

This is expressed more generally. A spectrometer according to a first embodiment (1) of the present invention comprises: accumulation means for accumulating M spectral data sets or time-domain data sets S1 (d1 to dN) to SM(d1 to dN) obtained by repeating the same measurement M times, each of the data sets having N data points; correlation computing means for finding correlations between sets of data points which are contained in the M spectral data sets or time-domain data sets S1(d1 to dN) to SM(d1 to dN), each of the sets consisting of data points having the same ordinal number, to thereby find a correlation data set C(c1 to cN) indicating correlation strengths about the data points of the ordinal numbers; and computing means for finding the product of an anticipated spectral data set or a time-domain data set Sav(d1 to dN) having the N data points and obtained from the accumulation means and the correlation data set C(c1 to cN). A measuring apparatus according to a second embodiment (2) of the present invention comprises: means for creating M data sets S (d1 to dN) to SM (d1 to dN) by repeating a measurement while varying at least one measurement parameter in M increments, each of the data sets having N data points; means for creating sets of the data points contained in the M data sets S1 (d1 to dN) to SM (d1 to dN) such that each of the sets S1 (dn) to SM (dn) contains data points of the same ordinal number; correlation computing means for finding a correlation data set C(c1 to cN) indicating correlation strengths about the data points of the ordinal numbers by finding correlations between data representing variations forecasted in response to variations in the parameter regarding the sets of the data points of the same ordinal numbers; and computing means for finding the product of an anticipated data set Sav (d1 to dN) which has N data points and which is obtained by an accumulation operation after correcting effects of variations in the parameter regarding the data sets S1(d1 to dN) to SM(d1 to dN) and the correlation data set C(c1 to cN) or the product of a separately measured data set So(d1 to dN) and the correlation data set C(c1 to cN).

Embodiment 7

The present embodiment is an expansion of Embodiment 6. On a direct observation axis, an observable signal is known as a single quantum signal. Therefore, in the same way as in Embodiments 2 and 3, the behavior of an NMR signal when the phase varies is represented by a straight line having a tilt of 1.

On the other hand, on an indirect observation axis, a multi-quantum signal can also be observed. As an example, with respect to an n-quantum signal, it is known that its behavior relative to the excitation phase (or observation phase) is multiplied by a factor of n. Where such a signal is observed, the present invention can be implemented by finding the correlation with the straight line having a tilt of n.

The operation is similar to the operation of Embodiment 6 except that the tilt of correlation is different.

Embodiment 8

The present embodiment is a combination of a technique of Embodiments 1-5 and a technique of Embodiments 6-7. Any one of Embodiments 1-5 is employed for processing related to a direct observation axis. Either Embodiment 5 or 7 is used for processing related to an indirect observation axis. Since the present embodiment relies only on a combination, the processing is similar to Embodiments 1-5 and 6-7.

Embodiment 9

In the description of the above Embodiments 1-8, a correlation strength is taken as a weight parameter. A spectrum obtained by accumulating spectra is then weighted. These steps are carried out in this order. Alternatively, individual original spectra not yet accumulated may be weighted and then accumulated.

The present invention can be applied to NMR spectroscopy. In addition, the invention can be applied to ESR spectroscopy and various kinds of electromagnetic spectroscopy employing X-rays, ultraviolet rays, visible light, infrared radiation, microwaves, or radio waves, and ion spectroscopy (such as mass spectrometry). Where the expression "data points" is replaced by a word "pixels", the invention is useful as image processing techniques for medical imaging equipment, electron microscopes, astronomical telescopes, radars, and so on.

Having thus described our invention with the detail and particularity required by the Patent Laws, what is desired protected by Letters Patent is set forth in the following claims.

The invention claimed is:

1. A measuring apparatus comprising:
    means for creating M data sets S1 (d1 to dN) to SM (d1 to dN) by repeating a measurement while varying at least one measurement parameter in M increments, each of the data sets having N data points;
    means for creating sets S1 (dn) to SM (dn) of the data points contained in the M data sets S1 (d1 to dN) to SM (d1 to dN) such that the data points of each one of the sets S1 (dn) to SM (dn) have the same ordinal number dn;
    correlation computing means for finding a correlation data set C(c1 to cN) indicating correlation strengths about the data points of the ordinal numbers by finding correlations between data representing variations forecasted in response to variations in the parameter regarding the sets S1(dn) to SM(dn); and
    computing means for finding a product of an accumulated or anticipated data set Sav(d1 to dN) which has N data points and which is obtained by an accumulation operation after correcting effects of variations in the parameter regarding the data sets S1(d1 to dN) to SM(d1 to dN) and the correlation data set C(c1 to cN) or a product of a separately measured data set So(d1 to dN) and the correlation data set C(c1 to cN).

2. A measuring apparatus as set forth in claim 1, wherein said measuring apparatus is an NMR spectrometer, an ESR spectrometer, an electromagnetic spectrometer employing X-rays, ultraviolet rays, visible light, infrared radiation, microwaves, or radio waves, a mass spectrometer, an instrument utilizing a charged-particle beam (including an electron microscope), or an imaging apparatus employing any of such instruments.

3. A measuring apparatus as set forth in claim 2, wherein said measuring apparatus is an NMR spectrometer, and wherein a combination of the varied parameter and data whose correlations and their strengths should be found is at least one of (1) a combination in which the parameter is the phase of a reference wave for a receiving system for observing an NMR signal or the phase of an excitation RF wave for exciting nuclei under observation and the data whose correlations should be found indicate the phases at data points of an actually measured NMR signal, (2) a combination in which the parameter is the intensity of an excitation RF wave and the data whose correlations should be found indicate the intensities at data points of an actually measured NMR signal, and (3) a combination in which the parameter is a center frequency of an excitation RF wave and the data whose correlations indicate a frequency position at which an actually measured NMR signal appears.

4. A measuring apparatus as set forth in claim 3, wherein said correlation strength is found relative to data measured concerning a direct observation axis used in one-dimensional NMR measurements or relative to data obtained concerning an indirect observation axis used in multidimensional NMR spectroscopy.

5. A method of processing and displaying data indicative of the molecular structure of a specimen, comprising the steps of:

performing a NMR measurement using at least one measurement parameter to obtain a data set containing N data points;

repeating the measurement while varying the parameter in M increments to obtain M data sets S1 (d1 to dN) to SM (d1 to dN);

creating sets S1 (dn) to SM (dn) of the data points contained in the M spectral data sets S1 (d1 to dN) to SM (d1 to dN) such that the data points of each one of the sets S1 (dn) to SM (dn) have the same ordinal number dn;

finding, with a computer, corrections between data representing variations forecasted in response to variations in the parameter regarding the sets S1 (dn) to SM (dn) to thereby find a correlation data set C (c1 to cN) indicating correlation strengths about the data points of the ordinal numbers; and finding and displaying, with a computer, a product of an accumulated or anticipated data set Say (d1 to dN) which has N data points and which is obtained by an accumulation operation after correcting effects of variations in the parameter and the correlation data set C (c1 to cN) regarding the data sets S1 (d1 to dN) to SM (d1 to dN) or a product of a separately measured data set So (d1 to dN) and the correlation data set C (c1 to cN).

* * * * *

UNITED STATES PATENT AND TRADEMARK OFFICE
CERTIFICATE OF CORRECTION

Page 1 of 1

PATENT NO.         : 8,798,949 B2
APPLICATION NO.    : 13/109165
DATED              : August 5, 2014
INVENTOR(S)        : Kiyonori Takegoshi It is certified that error appears in the above-identified patent and that said Letters Patent is hereby corrected as shown below:

In the Claims

Column 20, Line 10, Claim 5, delete "Say" and insert -- Sav --

Signed and Sealed this
Ninth Day of December, 2014

Michelle K. Lee
*Deputy Director of the United States Patent and Trademark Office*